United States Patent [19]

Nelson

[11] 4,446,140

[45] May 1, 1984

[54] METHOD AND COMPOSITION FOR TREATING MOUTH PAIN

[75] Inventor: Eric L. Nelson, Santa Ana, Calif.

[73] Assignee: Nelson Research & Development Company, Irvine, Calif.

[21] Appl. No.: 362,933

[22] Filed: Mar. 29, 1982

Related U.S. Application Data

[63] Continuation-in-part of Ser. No. 329,550, Dec. 10, 1981, which is a continuation of Ser. No. 140,493, Apr. 15, 1980, Pat. No. 4,316,888.

[51] Int. Cl.³ .......................................... A61K 31/485
[52] U.S. Cl. .................................... 424/260; 424/232
[58] Field of Search ........................ 424/232, 260, 256

[56] References Cited

PUBLICATIONS

*Handbook of Nonprescription Drugs,* Fifth Edition, Pub. by Amer. Pharm. Assoc., Wash. D.C., pp. 81, 82, 89, 90, 99–102, 105 & 104.

*Primary Examiner*—Frederick E. Waddell

[57] ABSTRACT

A method for treating mouth pain by administering to a human having such pain an effective mouth pain reducing amount of dextromethorphan, preferably as the hydrobromide.

6 Claims, No Drawings

METHOD AND COMPOSITION FOR TREATING MOUTH PAIN

RELATION TO EARLIER FILED APPLICATION

This application is a continuation-in-part of U.S. application Ser. No. 329,550 filed Dec. 10, 1981, which is in turn a continuation of U.S. application Ser. No. 140,493 filed Apr. 15, 1980, now U.S. Pat. No. 4,316,888.

BACKGROUND OF THE INVENTION

1. Field of the Invention

The invention relates to a method of treatment for mouth pain. More particularly the invention relates to a method for temporarily reducing mouth pain and discomfort in humans.

2. Background of the Prior Art

Mouth pain is pain or discomfort associated with the oral cavity, the teeth, gums and other mucosal surfaces of the lips, tongue and mouth resulting from known or unknown causes, e.g., toothache, denture irritations, canker sores, irritation related to inflamed gums, orthodontic tooth manipulation and appliances, oral surgery, etc.

Typical treatment for mouth pain is symptomatic relief with conventional analgesics such as aspirin or with oral anesthetics such as benzocaine and butacaine.

Dextromethorphan is an old compound used heretofore as an antitussive. It is marketed in a wide variety of "over-the-counter" (OTC) and prescription (Rx) products for relief of cough, typically as the hydrobromide. It is described in the art consistently as having no significant analgesic activity.

SUMMARY OF THE INVENTION

Notwithstanding the long established belief that dextromethorphan has no significant analgesic activity, it has now been discovered that dextromethorphan is useful in the treatment of mouth pain in the temporary reduction of such pain.

More particularly, the invention relates to a method of temporarily reducing pain and discomfort associated with mouth pain comprising administering to a human having mouth pain an effective, mouth pain reducing amount of dextromethorphan or a pharmaceutically active salt thereof. The preferred active compound is dextromethorphan hydrobromide.

The invention further relates to pharmaceutical compositions comprising an effective, mouth pain reducing amount of dextromethorphan and preferably dextromethorphan hydrobromide in combination with (1) a conventional analgesic, such as, for example, aspirin or acetaminophen, indomethacin, ibuprofen or naproxen; or (2) a conventional anesthetic, such as, for example, benzocaine or butacaine.

DETAILED DESCRIPTION OF THE INVENTION

Dextromethorphan (d-3-methoxy-N-methylmorphinan) is the d-isomer of the codeine analog of levorphanol; however, unlike the l-isomer, it has consistently been reported by the prior art as having no significant analgesic properties. The compound is well known in the art as a cough suppressant (antitussive) and is commercially available; e.g., U.S. Pat. No. 2,676,177 and Hafliger et al, Helv. Chim. Acta 39, 2053 (1956). The hydrobromide salt of dextromethorphan is widely commercially used as an "over-the-counter" (OTC) orally administered antitussive. It is also used as an antitussive in combination with antihistamines in prescription (Rx) products for cold remedies.

Dextromethorphan may be used in the present invention in daily dosage amounts between about 5 mg and 500 mg and preferably between about 10 mg and about 200 mg depending on the age and weight of the human to be treated and the severity of the mouth pain to be treated. A typical daily dosage amount varies between about 10 mg and about 200 mg and preferably between about 20 mg and 100 mg. For example, a typical dosage amount of dextromethorphan hydrobromide effective in temporarily reducing mouth pain in an adult human would be about 10 mg to about 50 mg administered in equal doses 1 to 4 times per day.

Combinations of dextromethorphan and conventional analgesics are preferred in the treatment of mouth pain. Analgesics suitable for use in combination with dextromethorphan include prostaglandin synthetase inhibitors such as aspirin, indomethacin and ibuprofen and other analgesics such as naproxen and acetaminophen. The amount of other analgesic to be used in combination with dextromethorphan is generally the amount conventionally used for treating mouth pain in humans.

Combinations of dextromethorphan and conventional oral anesthetics may also be used in treating mouth pain. Oral anesthetics suitable for use in combination with dextromethorphan include benzocaine, butacaine, phenol, sodium phenolate, etc. The amount of oral anesthetic to be used in combination with dextromethorphan is generally the amount conventionally used for treating mouth pain in humans.

For therapeutic use, dextromethorphan will normally be administered as a pharmaceutical composition in the basic form or in the form of an addition salt with a pharmaceutically acceptable acid and in association with a pharmaceutical carrier therefor. Such addition salts include those with hydrochloric, hydrobromic, hydriodic, sulphuric and maleic acids and preferably hydrobromic.

Other pharmacologically active compounds may, in certain cases, be included in the composition. Advantageously, the composition will be made up in a dosage unit form appropriate to the desired mode of administration, for example, as a tablet, capsule, sustained release type, oral suspension, or in a suitable formulation for conventional or sustained release topical administration.

The pharmaceutical compositions may be in a form suitable for oral use, for example, as tablets, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide a pharmaceutically elegant and palatable preparation. Tablets contain the active ingredient in admixture with nontoxic pharmaceutically acceptable excipients which are suitable for manufacture of tablets. These excipients may be, inert diluents, for example calcium carbonate, sodium carbonate, lactose, calcium phosphate or sodium phosphate; granulating and disintegrating agents, for example, maize starch, or alginic acid; binding agents for example, starch, gelatine or acacia, and lubricating agents, for example, magnesium stearate or stearic acid. The tablets may be uncoated or they may be coated by known techniques to delay disintegration and absorption in the gastrointestinal tract and thereby provide a sustained action over a longer period.

Formulations for oral use may also be presented as hard gelatine capsules wherein the active ingredient is mixed with an inert solid diluent, for example, calcium carbonate, calcium phosphate or kaolin, or as soft gelatine capsules wherein the active ingredient is mixed with an oil medium, for example, arachis oil, liquid paraffin or olive oil.

Aqueous suspensions contain the active ingredients in admixture with excipients suitable for the manufacture of aqueous suspensions. Such excipients are suspending agents, for example, sodium carboxymethyl cellulose, methylcellulose, hydroxypropylmethylcellulose, sodium alginate, polyvinylpyrrolidone, gum tragacanth and gum acacia; dispersing or wetting agents may be a naturally occurring phosphatide, for example, lecithin, or condensation products of an alkylene oxide with fatty acids, for example, polyoxyethylene stearate, or condensation products of ethylene oxide with long chain aliphatic alcohols, for example heptadecaethyleneoxycetanol, or condensation products of ethylene exide with partial esters derived from fatty acids and a hexitol, for example, polyoxyethylene sorbitol monooleate, or condensation product of ethylene oxide with partial esters derived from fatty acids and hexitol anhydrides, for example, polyoxyethylene sorbitan monooleate. The said aqueous suspensions may also contain one or more preservatives, for example ethyl-or n-propyl- p-hydroxy benzoate, one or more coloring agents, one or more flavoring agents and one or more sweetening agents, such as sucrose, saccharin, or sodium or calcium cyclamate.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present. Syrups and elixirs may be formulated with sweetening agents, for example glycerol, sorbitol or sucrose. Such formulations may also contain a demulcent, a preservative and flavoring and coloring agents.

The pharmaceutical compositions may be tableted or otherwise formulated so that for every 100 parts by weight of the composition there are present between 5 and 95 parts by weight of the active ingredient and preferably between 25 and 85 parts by weight of the active ingredient. The dosage unit form will generally contain between about 10 mg and about 500 mg of the active ingredients of the formula stated above.

From the foregoing formulation discussion, it is apparent that the composition of this invention is preferably administered topically or orally.

The scientific basis of the discovery set forth herein is not fully understood; however, it is believed that dextromethorphan is able to exert its pain reducing activity by acting upon specific pain mediating receptors in the body associated with endogenous peptides recently discovered to be involved in the mediation of pain, which peptides are known as enkephalins.

I claim:

1. A method of temporarily reducing pain and discomfort associated with mouth pain comprising administering to a human having mouth pain an effective mouth pain reducing amount of dextromethorphan or a pharmaceutically acceptable salt thereof.

2. The method of claim 1 wherein the dextromethorphan is administered in a daily dosage regimen of about 5 mg to about 500 mg.

3. The method of claim 1 wherein the dextromethorphan is administered in a daily dosage regimen of about 10 mg to about 200 mg.

4. The method of claim 1 wherein the dextromethorphan is administered in the form of its hydrobromide salt.

5. The method of claim 4 wherein the dextromethorphan hydrobromide is administered orally.

6. The method of claim 1 wherein the dextromethorphan is administered in an oral dosage form selected from the group consisting of a tablet, capsule, lozenge, syrup, suspension and elixir.

* * * * *